United States Patent [19]
Di Costanzo

[11] 3,989,823
[45] Nov. 2, 1976

[54] COMPOSITIONS FOR COMBATING NICOTINISM IN MAN
[76] Inventor: Francois Di Costanzo, 28 Rue Pauline Borghese, 92200 Neuilly, France
[22] Filed: Mar. 28, 1975
[21] Appl. No.: 562,922

[30] Foreign Application Priority Data
Mar. 29, 1974  France .............................. 74.11064

[52] U.S. Cl. .............................. 424/195; 424/254; 424/255; 424/263; 424/280
[51] Int. Cl.$^2$ .......................................... A61K 35/78
[58] Field of Search ..................................... 424/195

[56] References Cited
UNITED STATES PATENTS
2,600,700  6/1952  Smith .................................. 424/255
3,011,944  12/1961  Yamashita ......................... 424/255

OTHER PUBLICATIONS
Conn "Current Therapy" (1963) published by Saunders pp. 486–489 and 677.
Chemical Abstracts vol. 50, 14124d; vol. 52, 13842e; vol. 52, 14971g vol. 53, 3386d; vol. 53,3485b; vol. 55, 27660e and vol. 69, 9481g.
Kelly et al., Br. J. Addict. Jan. 1971, vol. 66. pp. 19, 20, 28 & 29 (Pergamor Press, Great Britain).

Primary Examiner—Donald B. Meyer
Attorney, Agent, or Firm—Browdy and Neimark

[57] ABSTRACT

Compositions for combating various drug habits.

These compositions contain as an essential active administration. an agent without toxicity, which at the same time is endowed with properties for modifying the gustative and olfactory sensations fo the patient, and sedative properties, comprising valerian extract, advantageously associated with tonic agents, for correcting the disturbed glucidic metabolism of the patient, agents for correcting neuritis and trembling resulting from deprivation of the toxic substance, and with ascorbic acid (in the adinistration forms intended for day administration) or with agents for combating insomnia (in the forms intended for evening or night administeration.

The compositions may be used in de-intoxication treatments and in particular for treating heavy smoking, by modifying the gustative and olfactory sensations fo the patient, and simultaneous treatment of disturbances due to the intoxication itself, psychological frustration disturbances and physical disturbances resulting from deprivation of the toxic substance.

9 Claims, No Drawings

COMPOSITIONS FOR COMBATING NICOTINISM IN MAN

BACKGROUND OF THE INVENTION

The present invention relates to novel compositions for combating the noxious effects and the habit effects which various toxic substances have on the human organism; the invention relates more particularly to novel compositions for combating severely heavy smoking.

It is known that the use and in particular the abuse of tobacco can give rise to two kinds of poisoning, namely acute poisoning and chronic poisoning.

While acute poisoning is rare, the discomforts experienced when first taking up smoking, with cephalalgia, vomiting and fits of giddiness representing a benign form of such poisoning, the situation is unfortunately quite different as regards chronic poisoning or nicotine poisoning, which takes on the principal features of drug habits: physical dependence, which, while it may be inconspicuous, nonetheless exists, as is proven by the symptoms involved when the smoker is deprived of tobacco, in particular hypoglycemia which causes the deprived smoker to suck sweets, and tobacco habit.

There are many signs of chronic poisoning, which occur in various forms, with a varying degree of acuteness according to the individual person:

respiratory syndrome:

Irritation of the pulmonary passages: coughing and expectorations, which occur in the morning at the beginning but then become permanent, and which are due to a reduction in motility of the tracheobronchial cilia, which becomes insufficient to reject the normal and pathological secretions.

Chronic rhino-pharyngitis with venous edema of the uvula, due to the numerous contractions of the soft palate caused by the effort of "sweeping" the air passages.

Thus, the respiratory syndrome of smokers can be described as follows: dyspnea, noisy and whistling breathing, pharyngeal constriction, thoracic algias, and frequency of respiratory infections.

As an effect in the longer term, there is the danger of cancer; in fact, on a statistical basis, cancer of the lung is twenty times more frequent in smokers.

The danger to the respiratory organs is greater when smoking cigarettes than when smoking cigars, and cigars are in turn more dangerous than a pipe.

DIGESTIVE SYNDROMES

Digestive disturbances are due to the ingestion of saliva charged with tar and nicotine, which irritate the mucous membranes, and to the properties of nicotine of reducing gastric vascularization by vasoconstriction, inhibiting gastric contractions of hunger, and reducing secretions. The inhibition of stomach contractions due to hunger in particular can last for 15 to 60 minutes after a single cigarette. This action at the thalamic level points to the action of a central mechanism similar to that which is observed with other stimulants, such as amphetamines.

These various effects give rise to the possibility of the occurrence of stomatitis, the possibility of dyspetic disturbances (in particular reduction in appetite), which explain why the chronic smoker grows thin, and the fact that some ulcers are made worse by tobacco abuse. It is for this reason, when poisoning stops, that appetite is fully recovered and the person suffers from constipation.

CARDIO-VASCULAR SYNDROME

High blood pressure due to nicotine poisoning is due to a direct vaso-motor effect, at the same time as adrenalin secretion.

The patient often complains of a reduction in local warmth at his extremities.

As on the other hand there is a certain degree of antagonism as between the effects of the adrenalin produced and heparin at the level of the hematoblasts, tobacco encourages the occurrence of atheroma and arteritis.

Nicotine poisoning oxycarbonemia causes harmful hypoxemia in those who suffer from coronary troubles and from respiratory insufficiencies; nicotine is harmful from the point of view of the heart only because it causes an increased load on the respiratory system; while the healthy person can tolerate such an excess load, it must be avoided by those who suffer from heart trouble and arteritis.

Heart disturbances are revealed by tachycardia, palpitations, arrythmia, extra-systoles, the occurrence of signs of a pseudo-angor, all these being symptoms which, in a healthy person, disappear when the intake of tobacco is stopped. The frequency of coronarities and infarcts of the myocardium is substantially higher in smokers than in non-smokers.

NERVOUS SYNDROME

Recent research has shown that, if taken in small doses, in most healthy subjects, tobacco acts, like alcohol, as a stimulant; however, repeated or moderate abuse by some delicate subjects results in nervous disturbances which are shown by trembling, dizziness, psychic depression, loss of memory, at the same time as increased tendency to fatigue due to hypoglycemia and an insufficiency of vitamin C, which are perhaps related to a latent suprarenal insufficiency.

To sum up, abuse of tobacco can result in the occurence of respiratory, circulatory and general disturbancesl; in the long term, there may be the dangers of cancer, in particular of the tracheobronchial system and the upper aero-digestive passages. Such dangers increase with the nature of what is smoked, namely cigarettes, cigars or pipe, their frequency and the manner of surrendering oneself to this drug habit, and depending on whether the smoke is or is not inhaled.

The harmful effect of tobacco being demonstrated, there results therefrom a certain number of counter-indications in various complaints: infarcts of the myocardium, cardiac insufficiency, acute rheumatic endocarditis, high blood pressure, arteriosclerosis, angina pectoris, pharyngitis, chronic rhinopharyngeal catarrh, pulmonary emphysema, pulmonary tuberculosis, gastro-duodenal ulcers, etc.

As it has been found that the smoker, like any person suffering from an intoxication, is generally incapable of stopping smoking, attempts have been made to suppress the toxic effects of tobacco without forcing the smoker to give up smoking. Thus, some types of cigarettes have been provided with filter tips which retain only 30% of the smoke. Similarly, some of the cigarettes which are made at present are produced with tobaccos whose content of nicotine, gum, wax and paraffin is substantially lower, up to a half less, than the content in tobaccos used for example about 20 years ago. However, as it is precisely the stimulating effects of nicotine which the smoker is generally seeking, smoking cigarettes with a reduced nicotine content has the result off increasing cigarette consumption.

Moreover, de-nicotinised cigarettes have been put on the market; however, the treatment to which the tobacco is subjected to extract the nicotine therefrom at the same time extracts its flavor, so that smokers do not generally enjoy de-nicotinized cigarettes.

Attempts at hybridizing the tobacco plant have effectively resulted in elimination of nicotine, while leaving the taste of tobacco in the plant, but growing such hybrids is faced with difficulties such that the prohibitive cost thereof virtually eliminates them from the market.

As it seems that the means of smoking without danger to health have not yet been discovered, it has been found necessary to propose means for de-intoxicating smokers who suffer from nicotine poisoning, for the purposes of curing such smokers of their vice.

These means can be essentially grouped in two categories:

They may comprise substitution substances for the intoxication agent, which, by virtue of the pharmacological similarity to nicotine and the similar effects which they have on the organism, give rise to a sensation of tobacco satiety which makes it possible to suppress or considerably reduce tobacco consumption;

They can comprise agents which are capable of modifying the gustative and olfactory sensations of the smoker in respect of tobacco, and give rise to disgust for tobacco.

Thus, compositions have been put forward which include substances replacing nicotine; however, some experimenters have been led to ask whether the substitution effect is long-lasting.

Moreover, the agents which are capable of modifying the gustative and olfactory sensations of the smoker, as proposed hitherto, in particular mineral or organic silver salts, alum or copper acetate, besides the fact that they are not totally without any toxic effect, are not capable either of correcting the disturbances suffered by the smoker (insufficient vitamin C and hypoglycemia in particular), or the disturbances resulting from cessation of smoking (character disorders, sleep disorders and physical disorders in particular).

DESCRIPTION OF THE INVENTION

Consequently, the aim of the present invention is to provide novel compositions capable of combating in man the harmful effects and the habit effects due to the use of toxic substances, in particular tobacco, which are better able to deal with the practical necessities than previously known substances striving for the same aim, in particular in that the proposed novel compositions in accordance with the present invention have a powerful effect as regards modifying the gustative and olfactory sensations of the intoxicated person, while simultaneously treating both the disturbances involved in the intoxication itself and the psychological frustration disturbances and physical disturbances which result from deprivation of the toxic substance.

The present invention concerns novel compositions capable of combating in man the harmful effects and the habit effects due to the use of toxic substances, in particular tobacco, characterized in that they contain as an essential active principle an agent without any toxicity, which at the same time is endowed with properties of modifying the gustative and olfactory sensations of the intoxicated person, and sedative properties, comprising valerian extract, advantageously associated with tonic agents, for correcting the disturbed glucidic metabolism of the patient, such as vitamin $B_1$, and/or with agents for correcting neuritis and trembling resulting from deprivation of the toxic substance, such as vitamin $B_6$, and/or with ascorbic acid and/or with agents for combating insomnia.

In an advantageous form of the compositions according to the present invention, the compositions contain agents for combating insomnia, when they are intended for evening or night administration.

In accordance with another advantageous embodiment of the compositions according to the present invention, these compositions contain ascorbic acid, in the absence of any agent for combating insomnia, when they are intended for administration in the day.

In accordance with a preferred form of the compositions according to the present invention, these compositions are in a form which can be administered orally, such as compressed tablets, pills and capsules.

In accordance with an advantageous form of the invention, the content, in the compositions according to the invention, of dry valerian extract is from 15 to 30% by weight.

The amount of agent for combating insomnia in the compositions according to the invention is preferably from 10 to 15% by weight.

The amount of ascorbic acid or vitamin C in these compositions is advantageously from 30 to 40% by weight.

When the tonic agent, for correcting hypoglycemia, which is contained in the compositions according to the present invention, is vitamin $B_1$, the latter is present in an amount of from 6.5 to 15% by weight.

When the agent in the compositions according to the invention, for preventing the trembling fits which are triggered off in the patient by being frustrated of the toxic substance, comprises vitamin $B_6$, this is present in a proportion of 30 to 55% by weight.

In accordance with the invention, the agent in the compositions according to the invention for combating insomnia advantageously comprises sodium secobarbital.

The therapeutic efficiency of the product as a de-intoxication agent is primarily linked to the presence of the valerian extract, in the compositions according to the present invention, the efficiency of the valerian extract being increased synergetically by the presence of:

vitamin C which compensates for the fall in the amount of ascorbic acid in the biological media of the smokers, and has a not inconsiderable sthenic effect;

vitamins of group B, which respond to any asthenia and neurotoxicity caused by nicotine (vitamin $B_1$) and/or its cardiovascular toxicity (vitamin $B_6$);

sodium secobarbital which, when present in small doses in the pills, compressed tablets, gelatin capsules, etc, administered before going to bed, makes it possible to induce sleep.

The valerian extract, which is totally without any toxicity, has long been used for treating neurasthenia, neuroses and psychic and sensory hyperexcitability.

The applicant has surprisingly found at present that the organoleptic properties of valerian have a therapeutic activity in respect of flavor, which triggers off orogustative and olfactory modifications which are opposed to the "smoke shock", and cause a distaste for tobacco.

The action of modifying the gustative and olfactory sensations of the patient under treatment, as produced by the valerian extract, is associated with a per se known calming action in respect of disturbances on being frustrated of the toxic substance, which primarily occur in the form of the anxiety-irritability-insomnia syndrome from which the patient suffers at the beginning of his cure.

Besides the above forms, the invention also comprises other forms which will be apparent from the following description.

The present invention concerns more particularly compositions capable of combating in man the harmful effects and the habit effects due to the use of toxic substances, in particular tobacco, in accordance with the preceding dispositions, the various forms of administration of such compounds, and the means used for the production thereof.

The invention will be better understood by means of the following description which refers to examples of compositions in accordance with the dispositions of the present invention.

It is to be understood however that these examples are given only way of example of the subject of the invention, and do not have any limiting character.

EXAMPLES

Example 1: Compositions intended for day administration

Formula D for producing 100 000 gelatin capsules:

| | |
|---|---|
| Dry extract of valerian | 5 kg |
| Coated ascorbic acid | 10 kg |
| Thiamine hydrochloride | 2.5 kg |
| Pyridoxine hydrochloride | 10 kg |
| Magnesium stearate | 0.570 kg |
| "AEROSIL R.200" (registered mark denoting microcrystalline silica) | 0.430 kg |
| Total : | 28.500 kg |

The valerian extract is first subjected to a drying operation for 24 hours in a place in which the relative humidity is lower than 60%, then the dry extract is incorporated in the above specified amount of "AEROSIL".

In addition, thiamine hydrochloride (vitamin $B_1$), pyridoxine hydrochloride (vitamin $B_6$) and magnesium stearate are sieved, and are incorporated in the dry valerian extract coated with "AEROSIL", then the coated ascorbic acid is added and the components are mixed until homogenized.

The mixture is distributed on a suitable machine, into gelatin capsules of size No. 1, in an amount of 285 mg per capsule.

These operations must be carried out in a place in which relative humidity is from 30 to 60% and temperature is equal to 20° C ± 2° C.

Example 2: Compositions intended for evening or night administration

Formula V for the production of 100 000 gelatin capsules:

| | |
|---|---|
| Dry extract of valerian | 5 kg |
| Sodium secobarbital | 2.5 kg |
| Thiamine hydrochloride | 2.5 kg |
| Pyridoxine hydrochloride | 10 kg |
| Magnesium stearate | 0.400 kg |
| "AEROSIL R.200" | 0.300 kg |
| Total : | 10.700 kg |

The valerian extract which has first been dried for a period of 24 hours in a place in which relative humidity is less than 60% is incorporated in the required amount of "AEROSIL" which coats it.

In addition, thiamine hydrochloride (vitamin $B_1$), pyridoxine hydrochloride (vitamin $B_6$), sodium secobarbital and magnesium stearate are sieved, and incorporated in the dry valerian extract which is coated with "AEROSIL", the components then being mixed until homogenized.

The homogenized mixture is then divided on a suitable machine, into gelatin capsules of size No. 1, with 207 mg in each capsule.

These operations must be carried out in a place in which relative humidity is from 30 to 60% and the temperature is 20° C ± 2° C.

It is of advantage for the compositions which are intended respectively for day administration and for evening or night administration to be introduced into gelatin capsules of different colors, for convenience in administration and use.

The efficiency of the compositions according to the present invention was revealed by means of pharmacological and clinical experiments, which will be referred to hereinafter, it being understood that these accounts are given solely by way of illustration of the subject of the invention, and do not constitute a limitation thereon.

I. Account of the pharmacological properties of the compositions according to the invention for combating in man the harmful effects and the habit effects due to the use of toxic substances.

A. Toxicological study

1. Demonstrating the harmlessness of a single administration by the digestive route in mouse and dog.
   a. In mouse:
      Administering in one lot the contents of 40 gelatin capsules of formulae D or V, which appear in Examples 1 and 2 above, per kg of body weight, gave rise to no signs of intolerance, nor had the slightest degree of toxic effect, in either a male or female mouse. Note should only be taken of the transitory occurrence of excitation under the effect of the capsules of formula D.
   b. In dog:
      Male and female dogs anesthetized by intra-venous injections of chloralose were the subject of the following recordings:
      blood pressure
      electrocardiograms in derivation $D_2$
      respiratory dynamism.
      The administration in one lot of a slurry prepared from the contents of 50 therapeutic doses of gelatin capsules of formula D or 100 therapeutic doses of gelatin capsules of formula V disturbed none of the physiological parameters set out above, registered in the dogs.

2. Sub-chronic toxicity in a rat.

30 young male Wistar rats weighing on average 130 g, and divided into three groups each of 10 animals, were the subject over a period of 15 days of daily treatment, under the following conditions:

rats Nos. 1 to 10: reference rats treated by a placebo (pseudo-colloidal solution of gum arabic, at a rate of 1 ml/100 g of body weight), rats Nos. 11 to 20: treated with the contents of one gelatin capsule of formula D per kg of body weight, suspended in the above carrier, rats Nos. 21 to 30: receiving under the same conditions a gelatin capsule of formula V, per kg of body weight.

Examination of the appearance and the behavior of the animals disclosed no difference as between the treated groups and the reference group.

No sign of intolerance was observed in the treated animals which received doses corresponding to 25 times the dose which it is intended should be administered in man, as regards capsules of formula D, and 50 times as regards capsules of formula V.

No death occurred in the course of the treatment.

At the end of the treatment, all of the animals were killed; under macroscopic examination no anomaly in the organs removed was found.

B. Pharmacological study

1. Influence on behavior in mice.

The aim of this test was to disclose the import of any action on the central nervous system. The test was carried out on groups of from 3 to 5 male Swiss mice each of 20 g, being either reference mice or mice treated by the digestive route at a rate of 1 gelatin capsule of formula D or V per kg of body weight.

Capsules of formula D:
  slight increase in the degree of curiosity of the animals (revealed by a larger number of visits to the board with holes),
  higher degree of reactivity to the touch,
  increase in muscular force.

Capsules of formula V:
  reduction in degree of curiosity and anxiety in the animals (test employing the board with holes),
  slight reduction in central temperature.

2. Protection against nicotine poisoning.

Two groups of male Swiss mice of 20 g, divided into groups of five animals, one of the groups receiving no preliminary treatment and the other group, having been treated daily for 12 days by the digestive route with 50 mg/kg of the compositions of formulae D or V, received on the 13th day increasing doses of nicotine tartrate, by way of intra-peritoneal injection.

Study of the degree of lethality occurring in the different groups indicated that the maximum dose of nicotine tartrate which is always tolerated, rises from 20 to 30 mg/kg when the animals have previously been treated by the digestive route with compositions containing valerian. Whereas the $DL_{50}$ is equal to 33.5 mg/kg in the reference animals, it rises to $DL_{50} = 38.5$ mg/kg in the animals which were first treated.

In addition, the survival time in respect of toxic doses is longer with the pretreated animals than the reference animals.

A second experiment in the course of which 200 mg/kg was administered daily for a period of 5 days to groups of 10 mice, in the form of the contents of 4 gelatin capsules of formula D or V, showed that the pretreated animals which on the 6th day received 35 mg/kg of nicotine tartrate intra-peritoneally were partially protected from the lethal effects of the nicotine tartrate.

II. Account of a clinical experiment carried out with the compositions according to the present invention.

The compositions used in this experiment are those described in Examples 1 and 2 above.

The de-intoxication cure, using compositions according to the present invention, was proposed for two groups of smokers:

First Group: 48 sick persons having substantial cardiovascular pathology, dominated by ischemiant arterial lesions.

Second Group: 32 smokers, volunteers, having no clinical complaint.

Posology:
  4 gelatin capsules of formula D per day, taken at fixed hours:
    after breakfast
    at 10 to 11 a.m.
    after lunch
    at 4 p.m.
  2 gelatin capsules of formula V per day, taken before going to bed.

Time of treatment:
  ≤ 3 weeks: 9 subjects
  3 weeks: 37 subjects
  1 month: 31 subjects
  ≥ 6 weeks: 3 subjects Criteria of observation:
  a. consumption of tobacco
  b. desire to smoke
  c. frustration symptoms connected to the cessation or reduction in the consumption of tobacco (represented by neurosensorial symptoms, nervous diathesis, insomnia, trembling, and asthenia; psychic symptoms, irritability and character and/or intellectual changes; and physical symptoms, coughing, expectoration, appetite and weight).
  d. the "valerian effect" represented by the gustative and olfactory changes spontaneously noted by the subject and triggered by the administration of valerian.

CONCLUSIONS

The efficiency of the compositions according to the invention in nicotine de-intoxication appears remarkable:

Taking the compositions results overall in a positive result in 66% of cases, while a 75% success rate is recorded in the group of sick persons having cardiovascular pathology, The desire to smoke is influenced in 70% of cases by the orogustative and olfactory changes triggered by the particular organoleptic properties of valerian, The tranquilizing effect on the frustration syndrome is beyond doubt: the neuro-sensorial signs induced by the cessation of intoxication are favorably influenced in 75% of cases, The clinical and biological tolerance of the compositions according to the invention is perfect, as shown by the operations of determining the biological constants.

It will be seen from the foregoing description that, whatever the forms of production and administration, there are obtained compositions which are capable of combating in man the harmful effects and the habit effects due to the use of toxic substances, in particular tobacco, which have substantial advantages over previously known products provided for the same purpose, in particular the advantage of achieving indisputable therapeutic progress on previously proposed de-intoxication cures, which on average achieve the following results:

overall: 33% success
individual psychotherapy: 41% success
group psychotherapy: 34% success
medications: 22% success

What I claim is:

1. A composition for combating nicotinism, comprising:
   10–15% by wt. dry extract of valerian in an amount sufficient to modify the gustatory and olfactory sensations,
   6.5–15% by wt. vitamin $B_1$ in an amount sufficient to correct disturbed glucidic metabolism;
   30–55% by wt. vitamin $B_6$ in an amount sufficient to correct neuritis and trembling resulting from the deprivation of nicotine;
   30–40% by wt. ascorbic acid in an amount sufficient to compensate for the fall in the amount of ascorbic acid in the biological media of smokers, and
   a sufficient quantity of pharmaceutically acceptable excipient to give 100%.

2. A composition in accordance with claim 1 in the form of an orally administrable tablet, gelatin capsule or pill.

3. A composition in accordance with claim 2 wherein said tablet, gelatin capsule or pill is coated with a gastro-resistant glaze.

4. A composition for combating nicotinism, comprising:
   10–15% by wt. dry extract of valerian in an amount sufficient to modify the gustatory and olfactory sensations;
   6.5–15% by wt. vitamin $B_1$ in an amount sufficient to correct disturbed glucidic metabolism;
   30–55% by wt. vitamin $B_6$ in an amount sufficient to correct neuritis and trembling resulting from the deprivation of nicotine;
   10–15% by wt. anti-insomnia agent in a quantity sufficient to induce sleep, and
   a sufficient quantity of pharmaceutically acceptable excipient to give 100%.

5. A composition in accordance with claim 4 wherein said anti-insomnia agent comprises sodium secobarbital.

6. A composition in accordance with claim 4 wherein said anti-insomnia agent comprises sodium secobarbital.

7. A composition in accordance with claim 4 in the form of an orally administrable tablet, gelatin capsule or pill.

8. Process for combating nicotinism in humans, comprising:
   orally administering in the daytime a composition comprising:
   10–15% by weight dry extract of valerian;
   6.5–15% by weight vitamin $B_1$;
   30–55% by weight vitamin $B_6$;
   30–40% by weight ascorbic acid; and
   a sufficient quantity of pharmaceutically acceptable excipient to give 100%;
   orally administering at night a composition, comprising:
   10–15% by weight dry extract valerian;
   6.5–15% by weight vitamin $B_1$;
   30–55% by weight vitamin $B_6$;
   10–15% by weight anti-insomnia agent; and
   a sufficient quantity of pharmaceutically acceptable excipient to give 100%;
   wherein the combined daily dose of said compositions is in an amount effective to combat nicotinism.

9. A method in accordance with claim 8 wherein said anti-insomnia agent comprises sodium secobarbital.

* * * * *